(12) United States Patent
Hayashi et al.

(10) Patent No.: US 7,025,778 B2
(45) Date of Patent: Apr. 11, 2006

(54) ENDOVASCULAR GRAFT WITH PRESSURE, TEMPERATURE, FLOW AND VOLTAGE SENSORS

(75) Inventors: Reid K. Hayashi, Santa Cruz, CA (US); Alfred Concemi, Flagstaff, AZ (US)

(73) Assignee: Endovascular Technologies, Inc., Santa Clara, CA (US)

(*) Notice: Subject to any disclaimer, the term of this patent is extended or adjusted under 35 U.S.C. 154(b) by 0 days.

(21) Appl. No.: 10/165,200

(22) Filed: Jun. 7, 2002

(65) Prior Publication Data

US 2003/0229388 A1 Dec. 11, 2003

(51) Int. Cl.
*A61F 2/06* (2006.01)

(52) U.S. Cl. ............... 623/1.34; 623/912; 623/1.16

(58) Field of Classification Search .......... 623/1.13, 623/1.23, 1.35, 1.34, 1.1, 66.1, 912, 1, 1.16; 600/485, 486
See application file for complete search history.

(56) References Cited

U.S. PATENT DOCUMENTS

| | | | |
|---|---|---|---|
| 3,240,207 A | 3/1966 | Barker et al. | |
| 4,815,472 A | 3/1989 | Wise et al. | |
| 4,834,101 A | 5/1989 | Collison et al. | |
| 4,846,191 A | 7/1989 | Brockway et al. | |
| 4,881,410 A | 11/1989 | Wise et al. | |
| 4,953,387 A | 9/1990 | Johnson | |
| 5,013,396 A | 5/1991 | Wise et al. | |
| 5,055,838 A | 10/1991 | Wise et al. | |
| 5,059,543 A | 10/1991 | Wise et al. | |
| 5,100,479 A | 3/1992 | Wise et al. | |
| 5,113,868 A | 5/1992 | Wise et al. | |
| 5,207,103 A | 5/1993 | Wise et al. | |
| 5,377,524 A | 1/1995 | Wise et al. | |
| 5,411,551 A | 5/1995 | Winston et al. | |
| 5,427,975 A | 6/1995 | Sparks et al. | |
| 5,531,121 A | 7/1996 | Sparks et al. | |
| 5,547,093 A | 8/1996 | Sparks | |
| 5,567,989 A | 10/1996 | Sim | |
| 5,598,847 A | 2/1997 | Renger | |
| 5,663,508 A | 9/1997 | Sparks | |
| 5,683,449 A * | 11/1997 | Marcade | 128/898 |
| 5,719,069 A | 2/1998 | Sparks | |
| 5,756,900 A | 5/1998 | Arie et al. | |
| 5,807,258 A | 9/1998 | Cimochowski et al. | |
| 5,915,281 A | 6/1999 | Sparks | |
| 5,932,809 A | 8/1999 | Sparks et al. | |

(Continued)

FOREIGN PATENT DOCUMENTS

EP 0 646 365 A1 4/1995

(Continued)

Primary Examiner—Bruce Snow
Assistant Examiner—Cheryl Miller
(74) Attorney, Agent, or Firm—Fulwider Patton LLP

(57) ABSTRACT

An endovascular graft having one or more sensors attached to its internal and external surface, one or more power sources attached to its external surface and one or more transmitters attached to its external surface, the sensors capable of measuring pertinent parameters and each transmitter capable of transmitting signals containing pertinent parameters to one or more receiving devices located outside the patient's body. The sensors may measure pressure, temperature, blood flow, electrical potential, or any combination thereof. The sensors may be attached at specific locations on the graft material, thereby providing pertinent parameters from critical points inside the vasculature, or may be attached to form an array of sensors over the internal and external surface of the graft material, thereby providing a complete profile of pertinent parameters throughout the vasculature covered by the endovascular graft.

27 Claims, 3 Drawing Sheets

U.S. PATENT DOCUMENTS

| | | | |
|---|---|---|---|
| 5,936,164 A | 8/1999 | Sparks et al. | |
| 5,967,986 A * | 10/1999 | Cimochoowski et al. | 600/454 |
| 6,015,387 A | 1/2000 | Schwartz et al. | |
| 6,053,873 A | 4/2000 | Govari et al. | |
| 6,109,113 A | 8/2000 | Chavan et al. | |
| 6,159,156 A | 12/2000 | Van Bockel | |
| 6,170,488 B1 | 1/2001 | Spillman, Jr. et al. | |
| 6,171,253 B1 | 1/2001 | Bullister et al. | |
| 6,206,835 B1 | 3/2001 | Spillman, Jr. et al. | |
| 6,231,516 B1 | 5/2001 | Keilman et al. | |
| 6,277,078 B1 * | 8/2001 | Porat et al. | 600/486 |
| 6,416,474 B1 * | 7/2002 | Penner et al. | 600/309 |
| 6,431,175 B1 * | 8/2002 | Penner et al. | 128/899 |
| 6,442,413 B1 * | 8/2002 | Silver | 600/345 |
| 6,475,170 B1 * | 11/2002 | Doron et al. | 600/587 |
| 6,551,303 B1 * | 4/2003 | Van Tassel et al. | 604/508 |
| 6,682,490 B1 * | 1/2004 | Roy et al. | 600/486 |
| 6,840,956 B1 * | 1/2005 | Wolinsky et al. | 623/1.13 |
| 2001/0027338 A1 * | 10/2001 | Greenberg | |
| 2002/0045921 A1 | 4/2002 | Wolinsky et al. | |
| 2002/0128546 A1 * | 9/2002 | Silver | |
| 2002/0183628 A1 * | 12/2002 | Reich et al. | |
| 2003/0004562 A1 * | 1/2003 | DiCarlo | |
| 2003/0125790 A1 * | 7/2003 | Fastovsky et al. | |

FOREIGN PATENT DOCUMENTS

| | | |
|---|---|---|
| EP | 0 897 690 A1 | 2/1999 |
| WO | WO 83/03348 | 10/1983 |
| WO | WO 98/29030 | 7/1998 |
| WO | WO 99/26530 | 6/1999 |
| WO | WO 00/32092 | 6/2000 |

* cited by examiner

ENDOVASCULAR GRAFT WITH PRESSURE, TEMPERATURE, FLOW AND VOLTAGE SENSORS

BACKGROUND OF THE INVENTION

This invention relates to the treatment of body lumens and, more particularly, to the endovascular placement of a prosthetic graft within vasculature for the purpose of repairing the same.

Ruptured abdominal aortic aneurysms (AAA) are a leading cause of death in the United States. Treatment options to repair AAA include conventional open surgery and implantation of an endovascular graft. Conventional open surgical repair of AAA involves major abdominal surgery with associated high rates of morbidity. Endovascular grafts have been developed to endoluminally bypass abdominal aortic aneurysms through minimally invasive surgery. Many patients that are unacceptable surgical risks for open repairs are eligible for endovascular graft implantation. Deployment of transfemoral, endovascular grafts to treat AAA is appealing for many reasons: avoidance of an abdominal incision, lack of aortic cross clamping, the potential for regional anesthesia, and a shortened hospital stay.

Untreated AAA has been shown to continue to expand until rupture, with an associated high mortality rate. Implantation of endovascular grafts have also been associated with high complication rates, including perioperative death, conversion to open repair, the need for further intervention, the need for hemodialysis, a failure to cure the AAA, and wound complications.

The inability to obtain or maintain a secure seal between the vessel wall and the endovascular graft is a complication unique to endovascular aneurysm exclusion. Because the term "leak" has been associated with aneurysm rupture following conventional surgery, the term "endoleak" has been proposed as a more definitive description of this complication. It is believed that persistent endoleaks result in continued aneurysm expansion, which may eventually lead to aneurysm rupture. Aneurysms that have been successfully excluded have shown a tendency towards a reduction in aneurysm diameter. Failure to properly exclude the aneurysm from systemic arterial blood pressure keeps the patient at risk of impending rupture. Endoleaks have been classified according to the source of the leaks. Current classifications of endoleaks include four categories. Type I endoleaks are "perigraft" or "graft-related" leaks that involve a persistent channel of blood flow due to inadequate or ineffective sealing at the ends of the endovascular graft, or between overlapping components of a modular system. Type II endoleaks are retrograde flow into the aneurysm sac from patent lumbar arteries, the inferior mesenteric artery, or other collateral vessels. Type III endoleaks result from fabric tears, graft disconnection, or graft disintegration. Finally, Type IV endoleaks are flow through the graft fabric associated with graft wall porosity or permeability. Preoperative patent side branches are not a good predictor of postoperative endoleaks.

A number of reported cases of aneurysm rupture following implantation of an endovascular graft have been reported. Some of the ruptures occurred in patients without a documented endoleak.

A number of studies have focused on measurement of pressure within the aneurysm sac following implantation of an endovascular graft, both in the human patient, an animal model, or an in vitro model. Properly implanted endovascular grafts have been shown to reduce the pressure within the aneurysm sac while an endoleak, with or without detectable blood flow, continues to pressurize the sac at pressures equivalent to the systemic arterial pressure. Animal studies utilizing a predictable rupturing aneurysm model have shown that non-excluded aneurysms will rupture. Thrombosed aneurysm sacs may still receive pressurization from a sealed endoleak and this continued pressurization keeps the aneurysm at risk for rupture.

Current methods of patient follow-up include arteriography, contrast-enhanced spiral computed tomography (CT), duplex ultrasonography, abdominal X-ray, and intravascular ultrasound. All of these methods are costly and involve invasive procedures that have associated morbidity. None of the imaging methods are completely successful in detecting endoleaks. Therefore, the potential exists for an endoleak to go undetected until eventual rupture. An increase in aneurysm diameter is detectable, and should be considered an indication of endoleak. To avoid aneurysm rupture an increase in aneurysm diameter must be detected in a timely fashion to identify patients in need of corrective surgical procedures.

An endovascular graft with the ability to measure pressure within the aneurysm sac and provide feedback to the physician could identify those patients with persistent pressurization of their aneurysm, and subsequent risk of rupture. Some physicians are advocating that the follow-up examinations of AAA patients focus on pressure measurements, but that this is not currently clinically feasible.

Accordingly, there exists a need for an endovascular graft that facilitates non-invasive measurement of pressure, as well as other pertinent parameters, within the aneurysm sac and along the endovascular graft itself as a means for identifying patients at risk for aneurysm rupture after the endovascular graft is implanted. The present invention addresses these and other needs.

SUMMARY OF THE INVENTION

Briefly and in general terms, the present invention is embodied in an endovascular graft with sensors attached thereto. The device will have the ability to be delivered endovascularly and measure pertinent parameters within the excluded AAA. The endovascular graft would have the ability to transmit data about intra-sac parameters to an external monitoring device. Patient follow-up would be less costly (conducted in the physician office), non-invasive, and more accurate, allowing prompt intervention in those patients most at risk for acute rupture. The invention would also allow for more frequent patient follow-up, increasing the potential to diagnose and treat aneurysms at risk before acute rupture. The invention is applicable to all applications of endovascular grafts to treat aneurysmal segments of blood vessels. It is contemplated that the invention may be used with all shapes of endovascular grafts known within the art.

In one embodiment, sensors are attached to the endovascular graft at the superior end, inferior end and midsection. Measurements of pertinent parameters and comparison of those measurements may allow early identification of areas of the patient's vasculature at risk for aneurysm rupture, thrombus formation, infection, inflamation or other anomalies without the need for invasive procedures.

In another embodiment, a pattern of sensors are attached to the endovascular graft such that they cover the interior and exterior of the graft. The pattern of sensors allow a complete profile of pertinent parameters along the endovascular graft to be obtained. Such a profile may provide more accurate identification of anomalies.

Sensors with pressure measurement capability may be used to detect pressure changes external the endovascular graft, in the aneurysm sac or in blood flow through the interior of the endovascular graft indicative of graft failure, graft kinking, or endoleak due to an inadequate seal between the endovascular graft and the vasculature. Sensors with temperature measurement capability may be used to detect temperature differentials associated with "hot spots" related to inflamation, infection or thrombus formation in the vessel. Sensors with the capability to measure oxygen and other blood constituents such as enzymes, proteins, and nutrients, may be used to detect minute blood flow indicative of endoleak. Sensors with the capability to measure electrical potential may be used to detect differences in potential associated with areas of the vessel at risk for thrombus formation.

An antenna or other data transmitter and a power source may be attached external the endovascular graft, allowing a physician or technician to monitor graft and vessel health without the need for an invasive procedure. The transmitter transmits measurements made by the sensors to a receiver located outside the patient's body.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

As shown in the exemplary drawings and for purposes of illustration, the invention is embodied in a prosthetic endovascular graft implant having the ability to measure pertinent parameters inside and outside the graft material and transmit the measurements to a receiver located external the patient within whom the endovascular graft is implanted. In one aspect, the invention includes a graft with sensors mounted on the external and internal surface that measure parameters such as pressure, temperature or voltage. In another aspect the invention includes a transmitter and energy source which facilitate transmission of parameters measured by the sensors to a receiver located outside the patient's body.

Figure 1:
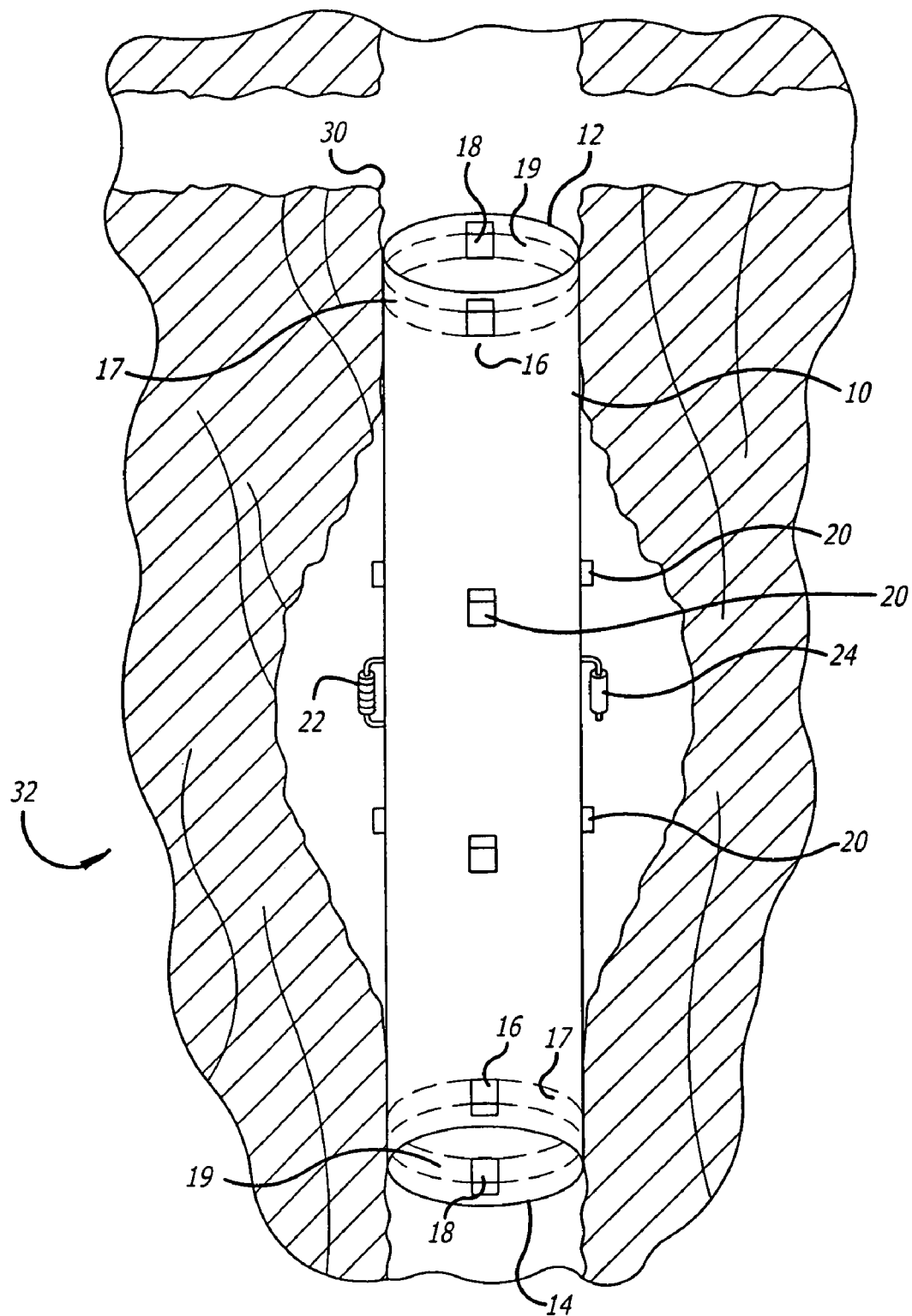
FIG. 1 is a partial cross-sectional view of one embodiment of the invention showing a generally tubular endovascular graft implanted across an aneurysm sac.

Referring to FIG. 1, an embodiment of the invention is shown in which a generally tubular, including flared or tapered, endovascular graft 10 having a superior end 12 and inferior end 14 is implanted in a body vessel 30 across an aneurysm sac 32 with the superior end 12 secured above the aneurysm and the inferior end 14 secured below the aneurysm. The endovascular graft 10 has sensors 16 attached external the superior 12 and inferior 14 ends. Additionally, the endovascular graft 10 has sensors 18 attached internal the superior 12 and inferior 14 ends. Furthermore, the endovascular graft 10 has sensors 20 attached external the midsection. Moreover, the endovascular graft 10 has a transmitter 22 and power source 24 attached external the graft material in the area where the graft traverses the aneurysm sac 32. The sensors 16, 18, 20 measure pertinent parameters inside and outside the endovascular graft and the power source 24 provides power for the transmitter 22 which transmits the measurements to a receiver (not shown) located outside the patient's body.

The transmitter 22, power source 24 and receiver (not shown) may be of any type known in the art of surgical implants or other systems utilizing miniaturized power sources and transmitters. The power source 24 and transmitter 22, for example, may be of the type used in pacemaker technology or passive power sources such as ultrasonically chargeable capacitors.

The sensors 16, 18, 20 of the invention shown in FIG. 1 may measure pressure. These measurements may be used as an aid in endovascular graft 10 placement or to identify anomalies that occur after endovascular graft 10 implantation before aneurysm rupture occurs.

The sensors 16 external the superior 12 and inferior 14 ends of the endovascular graft 10 may be used to detect changes in pressure resulting from blood leakage between the endovascular graft 10 and the vessel wall 30, an endoleak resulting from an inadequate seal between them. It is contemplated that sensors 17 may be located around the entire circumference of the superior 12 and inferior 14 ends of the endovascular graft 10, thereby allowing the exact location of an endoleak to be determined.

The sensors 18 internal the superior 12 and inferior 14 ends of the endovascular graft 10 may be used to measure inlet and outlet pressure of blood flow therethrough. A pressure drop indicates an anomaly such as kinking of the endovascular graft 10 or endoleak due to fabric tears or graft material disintegration. It is also contemplated that sensors 19 may be located around the entire circumference of the superior 12 and inferior 14 ends of the endovascular graft 10.

The sensors 20 external the midsection of the endovascular graft 10 may be used to measure pressure resulting from blood flow into the aneurysm sac 32, an indication that endoleak has occurred and there is a risk of aneurysm rupture. Because the sensors 20 are located in the area of the aneurysm sac 32, there are multiple sensors 20 disbursed over the graft material outer wall since local thrombus or calcification may shield one or more of the sensors 20 from blood pressure and render their measurements erroneous.

Figure 2:
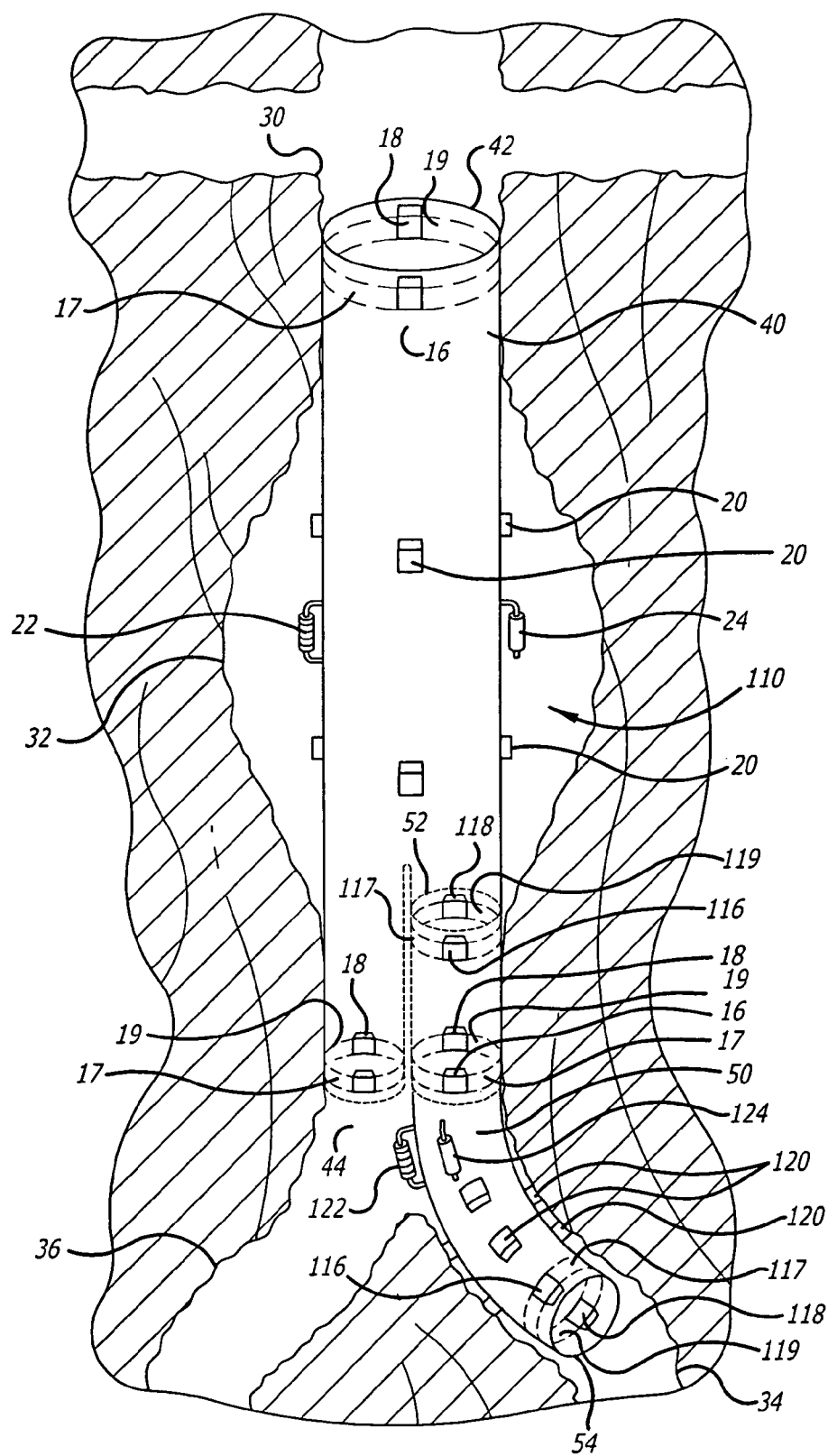
FIG. 2 is a partial cross-sectional view of an alternate embodiment of the invention shown in FIG. 1 showing a partially assembled bifurcated endovascular graft.

Referring to FIG. 2, the embodiment of the invention shown in FIG. 1 is applied to a bifurcated endovascular graft 110 of the type known within the art. The bifurcated endovascular graft 110 is assembled in-vivo from a tubular trunk portion 40 and two limb portions 50 (only one is shown). The bifurcated endovascular graft 110 is implanted in a body vessel 30 across an aneurysm sac 32 and into the contra-lateral 34 and ipsi-lateral 36 arteries using methods known within the art.

The trunk portion 40 has a superior end 42 adapted to be secured above the aneurysm and an inferior end 44 adapted to accept the limb portions 50. The trunk portion 40 has a transmitter 22, power source 24, and sensors 16, 17, 18, 19, 20 similar to those described with reference to FIG. 1.

Each limb portion 50 has a superior end 52 adapted to mate with the trunk portion 40 inferior end 44 and an inferior end 54 adapted to be secured to the ipsi-lateral 34 or contra-lateral 36 iliac artery. Each limb portion 50 also has a transmitter 122, power source 124, and sensors 116, 117, 118, 119, 120 similar to those described with reference to FIG. 1. The transmitter 122 and power source 124 facilitate transmission of parameters measured by the sensors 116, 117, 118, 119, 120 to a receiver (not shown) outside the patient's body.

The functions of some of the sensors are slightly different than those previously described with reference to a tubular endovascular graft. The sensors 116 external the superior 52 end of a limb portion 50 may be used to detect pressure changes resulting from blood leakage between the limb portion 50 and the trunk portion 40, an endoleak resulting from an inadequate seal between the limb portion 50 superior end 52 and trunk portion 40 inferior end 14. The sensors 116 external the inferior 54 end of a limb portion 50 may be used to detect pressure changes resulting from blood leakage between the limb portion 50 and the ipsi-lateral 34 or contra-lateral 36 iliac artery wall, an endoleak resulting from an inadequate seal between the limb portion 50 inferior end 54 and vessel 30. The sensors 118 internal the superior 52 and inferior 54 ends of a limb portion 50 may be used to measure inlet and outlet pressure of blood flow therethrough, with a pressure drop indicating an anomaly such as kinking of the limb portion 50 or endoleak due to fabric tears or graft material disintegration. The sensors 120 external the midsection of the limb portion 50 may be used to measure pressure resulting from blood flow between the limb portion 50 and the wall of the ipsi-lateral 34 or contra-lateral 36 iliac artery, an indication that endoleak has occurred due to inadequate mating of the limb portion 50 superior end 52 and the trunk portion 40 inferior end 44.

Alternatively, the sensors of the invention shown in FIGS. 1 and 2 may measure temperature. Differences in temperature may identify "hot spots" associated with infection, inflammation, thrombus formation or other anomalies that indicate an increased risk for aneurysm rupture. Methods known in the art of pathology and physiology may be used to relate temperature to changes in the vessel walls within which the endovascular graft is implanted.

Alternatively, the sensors of the invention shown in FIGS. 1 and 2 may detect blood flow by measuring oxygen or other constituents, such as enzymes, proteins and nutrients, which are altered by the presence of blood flow. Such sensors may allow detection of minute blood flow, often missed by conventional imaging modalities, and, therefore, allow endoleaks to be detected earlier. One method is to obtain a baseline of the constituents upon implantation of the endovascular graft. Thereafter, changes in the amount of the measured constituents may be used to identify anomalies.

Alternatively, the sensors of the invention shown in FIGS. 1 and 2 may measure electrical potential. Changes in electrical potential may identify areas of the patient's vasculature that are at risk for thrombus formation.

It is contemplated that the number of transmitters, power sources and sensors shown in FIGS. 1 and 2 may be varied to meet the requirements of the individual patient. It is further contemplated that sensors which measure different pertinent parameters may be used together. Moreover, it is contemplated that the invention shown in FIGS. 1 and 2 may be utilized in any type of endovascular graft implant known in the art.

Figure 3:
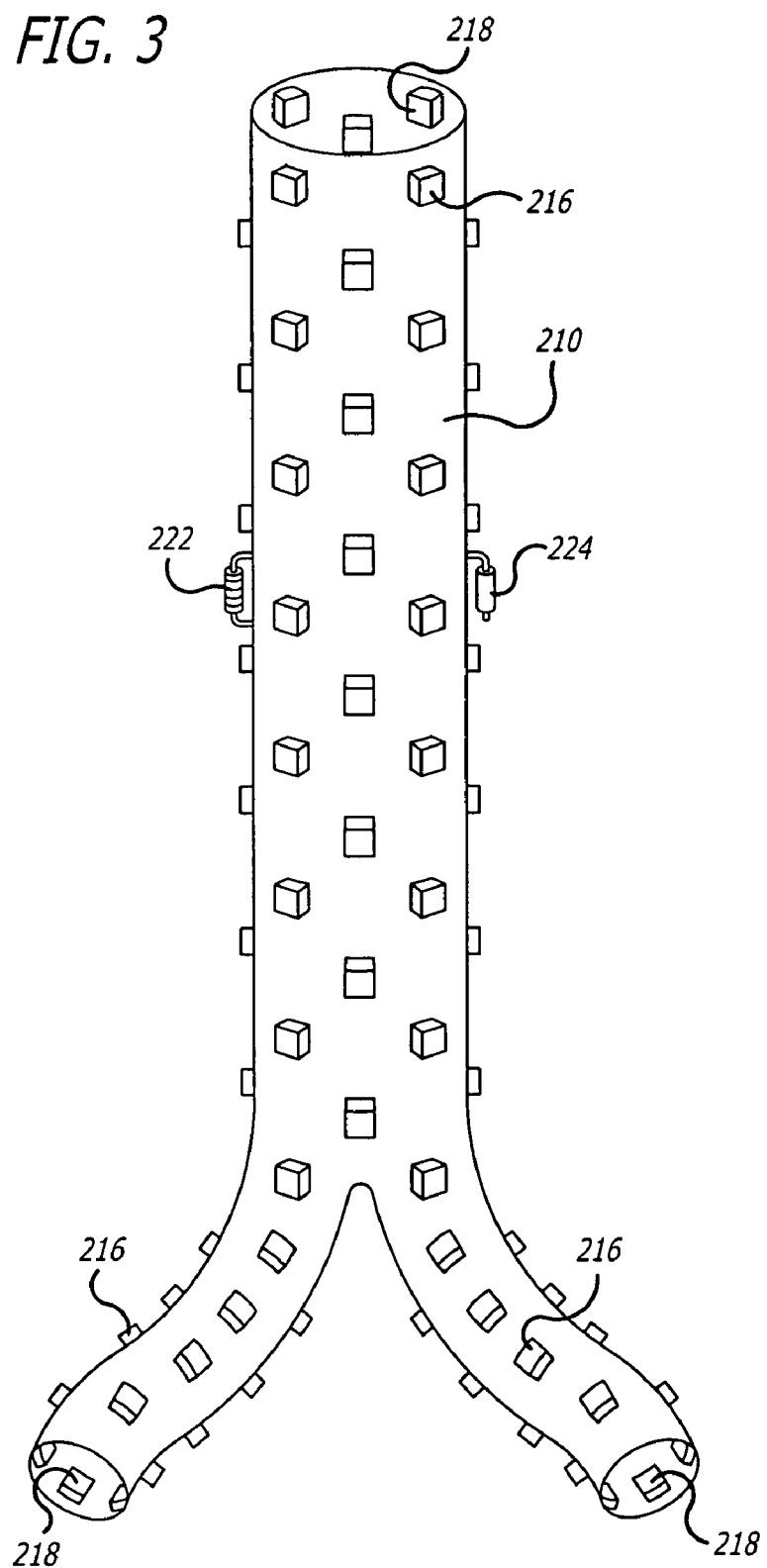
FIG. 3 is a perspective view of another embodiment of the invention showing a bifurcated endovascular graft having an array of sensors on the external and internal surfaces of the graft material.

Referring to FIG. 3, another embodiment of the invention is shown in which miniature sensors 216, 218 are arranged as an array covering the interior and exterior of the surface of the endovascular graft 210. The array of sensors 216, 218 provides a complete profile of pertinent parameters over the entire surface of the endovascular graft and, therefore, facilitates better identification of anomalies. The transmitter 222, power source 224 and external receiver (not shown) allow the measured parameters to be received and monitored outside the patient's body. The array of sensors 216, 218 may spiral around the graft material in between the weaves of fabric and consist of a strip of sensors, continuous strip of wire or other apparatus known in the art.

It is contemplated that the location and number of transmitters, power sources and sensors shown in FIG. 3 may be varied to meet the requirements of the individual patient. It is further contemplated that the array of sensors 216, 218 may contain sensors capable of measuring pressure, temperature, blood flow, electrical potential, or any combination thereof. Moreover, it is contemplated that the invention shown in FIG. 3 may be utilized in any type of endovascular graft implant known in the art.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A modular endoluminal prosthesis for repairing vasculature in the area of an aneurysm sac, comprising:
 a first endovascular graft component; and
 a second endovascular graft component configured to be delivered within vasculature separate from the first endovascular graft component, the second endovascular graft component including mating structure that accomplishes mating the second endovascular graft component to the first endovascular graft component in vasculature and having one or more sensors attached at a juncture between the first endovascular graft component and the second endovascular graft component, wherein the sensors of the second endovascular graft component detect parameters in the aneurysm sac relating to an endoleak at the juncture of the first endovacular graft and the second endovascular graft.

2. The prosthesis of claim 1, further comprising:
 one or more power sources attached to external surfaces of the first and second endovascular graft components; and
 one or more transmitting devices attached to the first and second endovascular graft components, each transmitting device capable of transmitting signals containing the parameters measured by one or more sensors to a location outside a patient's body.

3. The prosthesis of claim 2, further comprising one or more receiving devices located outside a patient's body, each receiving device capable of receiving signals transmitted by one or more transmitters.

4. The prosthesis of claim 2, wherein each power source is attached to a midsection of one of the first and second endovascular graft components.

5. The prosthesis of claim 2, wherein each transmitter is attached to a midsection of one of the first and second endovascular graft components.

6. The prosthesis of claim 1, the first endovascular graft component further comprising one or more sensors attached thereto.

7. The prosthesis of claim 1, wherein one of the first and second endovascular graft components is generally tubular and each have a superior end, an inferior end and a midsection.

8. The prosthesis of claim 1, wherein at least one sensor is located on an internal surface of one of the first and second endovascular graft components.

9. The prosthesis of claim 1, wherein sensors cover substantially a circumferential area of an internal surface of one of the first and second endovascular graft components.

10. The prosthesis of claim 1, wherein at least one sensor is located on an external surface of one of the first and second endovascular graft components.

11. The prosthesis of claim 1, wherein sensors cover substantially a circumferential area of an external surface of one of the first and second endovascular graft components.

12. The prosthesis of claim 1, wherein one or more sensors are located on an external surface of one or more of the endovascular graft components at a midsection thereof.

13. The prosthesis of claim 1, wherein the first endovascular graft component has a trunk portion and two or more limb portions.

14. The prosthesis of claim 13, wherein at least one sensor is located on an internal surface of the first endovascular graft component.

15. The prosthesis of claim 13, wherein sensors cover substantially a circumferential area of an internal surface of the first endovascular graft component.

16. The prosthesis of claim 13, wherein at least one sensor is located on an external surface of each limb portion.

17. The prosthesis of claim 13, wherein sensors cover substantially a circumferential area of an external surface of the first endovascular graft component at superior and inferior ends of each limb portion.

18. The prosthesis of claim 13, wherein one or more sensors are located external the first endovascular graft component at a midsection of each limb portion.

19. The prosthesis of claim 1, wherein one or more of the sensors measure pressure.

20. The prosthesis of claim 1, wherein one or more of the sensors measure temperature.

21. The prosthesis of claim 1, wherein one or more of the sensors measure a constituent altered by the presence of minute amounts of blood flow.

22. The prosthesis of claim 21, wherein the constituent measured is oxygen.

23. The prosthesis of claim 21, wherein the constituent measured is an enzyme.

24. The prosthesis of claim 21, wherein the constituent measured is a protein.

25. The prosthesis of claim 21, wherein the constituent measured is a nutrient.

26. The prosthesis of claim 1, wherein one or more of the sensors measure electrical potential.

27. The prosthesis of claim 1, wherein one or more of the sensors measure a parameter related to the attachment between the first and second endovascular graft components.

* * * * *

UNITED STATES PATENT AND TRADEMARK OFFICE
CERTIFICATE OF CORRECTION

PATENT NO. : 7,025,778 B2
APPLICATION NO. : 10/165200
DATED : April 11, 2006
INVENTOR(S) : Hayashi et al.

It is certified that error appears in the above-identified patent and that said Letters Patent is hereby corrected as shown below:

On the title page, item 56, under References Cited, please add under "U.S. Patent Documents" the following:

| | | |
|---|---|---|
| 2,634,721 | 5/1951 | Greenwood, Jr. |
| 3,888,708 | 6/1975 | Wise et al. |
| 4,732,874 | 3/1988 | Sparks |
| 5,000,049 | 3/1991 | Cooper et al.. |
| 5,213,999 | 5/1993 | Sparks et al. |
| 5,250,461 | 10/1993 | Sparks |
| 5,250,837 | 10/1993 | Sparks |
| 5,262,127 | 11/1993 | Wise et al. |
| 5,296,255 | 3/1994 | Gland et al. |
| 5,314,458 | 5/1994 | Najafi et al. |
| 5,343,064 | 8/1994 | Spangler et al. |
| 5,385,709 | 1/1995 | Wise et al. |
| 5,417,235 | 2/1995 | Wise et al. |
| 5,663,508 | 9/1997 | Sparks |
| 5,706,565 | 1/1998 | Sparks et al. |
| 5,735,887 | 4/1998 | Barreras, Sr. et al. |
| 5,831,162 | 11/1998 | Sparks et al. |
| 5,929,497 | 7/1999 | Chavan et al. |
| 5,967,989 | 10/1999 | Cimochowski et al. |
| 5,976,994 | 11/1999 | Nguyen et al. |
| 5,989,445 | 11/1999 | Wise et al. |
| 5,992,769 | 11/1999 | Wise et al. |

UNITED STATES PATENT AND TRADEMARK OFFICE
CERTIFICATE OF CORRECTION

PATENT NO. : 7,025,778 B2  Page 2 of 2
APPLICATION NO. : 10/165200
DATED : April 11, 2006
INVENTOR(S) : Hayashi et al.

It is certified that error appears in the above-identified patent and that said Letters Patent is hereby corrected as shown below:

| | | |
|---|---|---|
| 6,022,756 | 2/2000 | Sparks et al. |
| 6,035,714 | 3/2000 | Yazdi et al. |
| 6,062,461 | 5/2000 | Sparks et al. |
| 6,092,530 | 7/2000 | Weissman et al. |
| 6,136,212 | 10/2000 | Mastrangelo et al. |
| 6,140,144 | 10/2000 | Najafi et al. |
| 6,140,740 | 10/2000 | Porat et al. |
| 6,167,757 B1 | 1/2001 | Yazdi et al. |
| 6,169,321 | 1/2001 | Nguyen et al. |
| 6,197,965 B1 | 3/2001 | Penner et al. |
| 6,232,150 B1 | 5/2001 | Lin et al. |
| 6,237,398 B1 | 5/2001 | Porat et al. |
| 6,239,724 B1 | 5/2001 | Doron et al. |
| 6,286,369 B1 | 9/2001 | Yazdi et al. |
| 6,300,632 B1 | 10/2001 | Liu et al. |

On the title page, item 56, under Reference Cited, please add under "Foreign Patent Documents" the following:

WO 99/42039    8/1999
WO 01/36014 A2    5/2001

Signed and Sealed this

Twelfth Day of September, 2006

JON W. DUDAS
*Director of the United States Patent and Trademark Office*